US006732379B2

(12) United States Patent
Lebherz

(10) Patent No.: US 6,732,379 B2
(45) Date of Patent: May 11, 2004

(54) EAR PROTECTION DEVICE

(76) Inventor: Eugenia Fripp Ducker Lebherz, 1011 Shipman La., McLean, VA (US) 22101

( * ) Notice: Subject to any disclaimer, the term of this patent is extended or adjusted under 35 U.S.C. 154(b) by 0 days.

(21) Appl. No.: 10/098,554

(22) Filed: Mar. 18, 2002

(65) Prior Publication Data

US 2002/0170106 A1 Nov. 21, 2002

Related U.S. Application Data

(60) Provisional application No. 60/276,383, filed on Mar. 19, 2001.

(51) Int. Cl.[7] .................................................. A42B 1/06
(52) U.S. Cl. ......................................................... 2/209
(58) Field of Search ........................ 2/209, 423, 209.3, 2/916, 918, 174, 181, DIG. 11

(56) References Cited

U.S. PATENT DOCUMENTS

| | | | | | |
|---|---|---|---|---|---|
| 1,945,110 | A | * | 1/1934 | Gordon | 2/209 |
| 1,991,982 | A | * | 2/1935 | Hodges | 2/174 |
| 2,021,144 | A | * | 11/1935 | Beck | 2/174 |
| 2,070,216 | A | * | 2/1937 | Rosenberg | 2/209 |
| 2,405,326 | A | * | 8/1946 | Plotsky | 2/209 |
| 2,456,167 | A | * | 12/1948 | Arkus | 2/209 |
| 3,184,758 | A | * | 5/1965 | Hirsch | 2/209 |
| 3,229,308 | A | * | 1/1966 | Jensen | 2/209.3 |
| 3,340,542 | A | * | 9/1967 | Greenwald | 2/209.11 |
| 4,802,245 | A | * | 2/1989 | Miano | 2/209 |
| 4,805,239 | A | * | 2/1989 | Ciago | 2/24 |
| 5,023,954 | A | * | 6/1991 | Lyons | 2/174 |
| 5,038,412 | A | * | 8/1991 | Cionni | 2/209 |
| 5,058,606 | A | * | 10/1991 | Malkoff | 128/864 |
| 5,423,091 | A | * | 6/1995 | Lange | 2/181 |
| 5,963,989 | A | * | 10/1999 | Robertson | 2/411 |
| 6,189,151 | B1 | * | 2/2001 | Curtis | 2/171 |
| 6,205,590 | B1 | * | 3/2001 | Gorman | 2/181 |
| 6,227,011 | B1 | * | 5/2001 | Cortinovis | 66/171 |
| D446,609 | S | * | 8/2001 | Hill | D29/112 |
| 6,401,255 | B1 | * | 6/2002 | Douglas | 2/207 |

OTHER PUBLICATIONS

The Company Store, Our Down Velcro Headband Sep. 20, 1988.*

* cited by examiner

Primary Examiner—Rodney M. Lindsey

(57) ABSTRACT

There is provided an ear covering device to be worn over the ears of an individual in such a manner as to cup over the ears and to extend in a contoured manner at such an angle as to fit securely around the front of the individual's head along the very edge of the forehead at the hairline and furthermore to extend in a contoured manner at such an angle as to fit securely around the back of the individual's head along the very edge of the neck at the hairline. These ear coverings are constructed of a soft and pliable material or fabric, single or plural layers that expand for the comfort of the individual, for the purpose of keeping the ear protectors in place and for the ease of putting on and removing the ear protectors. These ear protectors can be constructed with the option of an opening with a fastening device on each end that adopts to cooperate in securing the ends together. When not in use, these comfortable and non-bulky Ear Protection Devices fold to the size of a pocket-handkerchief and will fit nicely into a coat pocket.

7 Claims, 6 Drawing Sheets

EAR PROTECTION DEVICE

CROSS-REFERENCE TO RELATED APPLICATIONS

I wish to claim the benefit of the filing date of a Provisional Patent for the same invention.

| Application No.: | 60/276,383 |
|---|---|
| Filing Date: | 03/19/2001 |

The Provisional Patent Application referenced above bore the title Earmuff/Headgear. It is the same invention as the present application.

FIELD OF SEARCH

| Class | Subclass |
|---|---|
| 2 | 208 |
| 2 | 209 |
| 2 | 175.3+ |
| D29 | 112 |
| D02 | 865+ |

REFERENCES CITED
U.S. Pat. Documents

| | | | |
|---|---|---|---|
| 794,559 | July 11, 1905 | Smith | 2/208 |
| 1,274,842 | Aug. 6, 1918 | Basch | D29/112 |
| 1,945,110 | Jan. 30, 1934 | Gordo | 2/209 |
| 2,070,216 | Feb. 9, 1937 | Rosenberg | 2/209, D29/112 |
| 2,361,963 | Nov. 7, 1944 | Rosenblatt | 2/209, D29/112 |
| 2,456,167 | Dec. 14, 1948 | Arkus | 2/209 |
| 2,504,826 | April 15, 1950 | Goldman | 2/209, D29/112 |
| 2,609,544 | Sept. 9, 1952 | Berg | 2/209, D29/112 |
| 2,693,599 | Nov. 9, 1954 | Berg | 2/209, D29/112 |
| 2,738,514 | Mar. 20, 1956 | Gondell | 2/209, D29/112 |
| 4,037,273 | July 26, 1977 | Labaire | 2/209, D29/112 |
| 4,133,052 | Jan. 9, 1979 | Hodgman | 2/209 |
| 4,682,374 | July 28, 1987 | Geiser | 2/209 |
| 4,802,245 | Feb. 7, 1989 | Miano | 2/208, 2/209 |
| 4,805,239 | Feb. 21, 1989 | Clago | 2/209 |
| 4,864,619 | Sept. 5, 1989 | Spates | 381/25 |
| 4,918,757 | April 24, 1990 | Janssen, et al | 2/209.3 |
| 5,023,954 | June 18, 1991 | Lyons | 2/209 |
| 5,038,412 | Aug. 13, 1991 | Cionni | 2/209 |
| 5,058,606 | Oct. 22, 1991 | Malkoff | 2/209 |
| 5,257,420 | July 31, 1992 | Byrne | 2/209 |
| 5,835,609 | Nov. 10, 1998 | LeGette, et al. | 2/209 |

BACKGROUND OF INVENTION

The present invention relates to ear coverings for the purpose of protecting the ears of an individual from the elements. The intention of the covering is to fit comfortably and securely over the ears and around the edges of the front and back hairline of the individual's head when being worn. This present invention, depending on the material or fabric chosen to construct the device, is appropriate for formal wear, for casual wear, for the athlete or the construction worker wearing a safety helmet, and for the jogger or an individual participating in almost any outdoor sport.

Generally, previously patented devices that cover an individual's ears for protection are hard on the appearance of the individual's hair. Many of these previously patented devices press tightly against the individual's ears, rendering such devices uncomfortable to wear for long periods of time. They are often too bulky or uncomfortable to wear along with a safety helmet; and many are bulky to carry when not being worn.

This present invention does not interfere with an individual's hairstyle because the bands connecting the ear cups go along the edge of the hairline of the individual and not on top of the hair. The present invention cups over the individual's ears, contouring along the front and back hairline, and does not press tightly against the individual's ears and is comfortable even when worn for long periods of time. And because the present invention is constructed from soft and pliable material or fabric, it can be worn comfortably under a safety helmet and the device can be folded or crushed then fitted neatly into the pocket of the individual when the device is not being worn.

Some of these previously patented ear protection devices are known as "ear muffs" and are represented in part by U.S. Pat. No. 5,551,089 to Jenna Whidden. These "ear muffs" generally include a band that extends across the top of an individual's head with the ear covers attached at the ends of the band.

There are previously patented ear protection devices referred to as "Sweatbands" and "Headbands" and represented in part by U.S. Pat. No. 5,257,420 to Richard Byrne, Jr. and U.S. Pat. No. 4,918,757 to Jenssen, et al. These devices generally have a continuous band going over the front of the individual's hair, across the ears and along the hairline at the neck. These devices generally press tightly against the ears of the individual making them uncomfortable with time and they are typically hard on the appearance of the individual's hairstyle when removed.

U.S. Pat. No. 5,835,609 to LeGette, et al. represents in part a style of "Ear Protection Device" that fits across the back of the head at the neck, extending to each ear with an ear protection covering. This device uses pressure to stay in place on the individual's head and cannot be worn with safety helmets.

Even with the existence of many types of ear protection devices, there is still a need for a device that has the features of the present invention.

BRIEF SUMMARY OF THE INVENTION

The present invention relates to the covering for an individual's ears for the purpose of protection from the elements, namely the cold and the wind.

There are many already patented devices that may offer the same protection but have the problem of being too bulky, too uncomfortable when worn for any length of time and generally, after being worn, leave the hairstyle of the individual in a mess. This invention conquers all of these problems and has even more to offer.

This invention is not bulky and may be so obscure as to go unnoticed when worn by an individual with long hair. Size and flexibility of fabric or material used to construct this invention make it possible to remove this device and conveniently put in into a coat pocket or some other convenient spot when not in use.

This invention is comfortable even when worn for long periods of time. This invention is constructed of soft and pliable material or fabric and because of the way it fits the head very little stretch, not tight, is needed to keep this device comfortably in place. This invention does not mash or press the ears against the head but instead the ears remain in their normal position. This invention can even be worn simultaneously with ear jewelry because it fits so gently over the ears.

The hair of an individual wearing this ear protection device is not changed, bothered or messed up because this device does not go over the hair but goes around the hairline in the front and in the back.

Because the front and the back bands of this invention are contoured to fit the shape of the human head and to cup over the ears, this device is secure even while participating in sports such as jogging, skiing, biking or even playing tennis.

Because of the way this device fits and because it is not bulky, it can even be comfortably worn with a sporting or workplace safety helmet or hardhat. The majority of safety helmets leave the ears exposed to the elements while protecting the head from injury. This device can be worn in conjunction with helmets without interfering with the performance of the helmet or being uncomfortable to the individual wearing both.

Depending on the color and style of material or fabric used to construct this Ear Protection Device, this invention can be attractively worn in cold or windy weather for out-of-doors-formal occasions such as Presidential Inaugurations or to and from formal indoor occasions. All with no fear of messing up one's hair for the event.

There is a real need for this invention. In many situations individuals will face the cold and the wind with unprotected ears and generally because the advantages of this invention are not available in the presently patented ear protection devices as referred to in this summary.

DETAILED DESCRIPTION OF THE INVENTION

Figure 1:
FIG. 1 is the view of an individual wearing the ear protection device.

In FIG. 1 the individual pictured is wearing this invention, an Ear Protection Device. The outside of the invention facing away from the individual is indicated by the numeral 1. This invention goes all the way around the head of an individual as it follows the hairline across the forehead, over each ear in a cupping manner and then along the neck hairline in the back of the head of an individual.

Since this invention is circular, only one side can be seen in a view and the opposite side is always a mirror image of the pictured views.

The pictured individual in FIG. 1 is lifting her hair with her hand to show this device, otherwise the hair would fall over the Ear Protection Device and it would be barely visible. This device is unobtrusive in the world of fashion.

Figure 2:
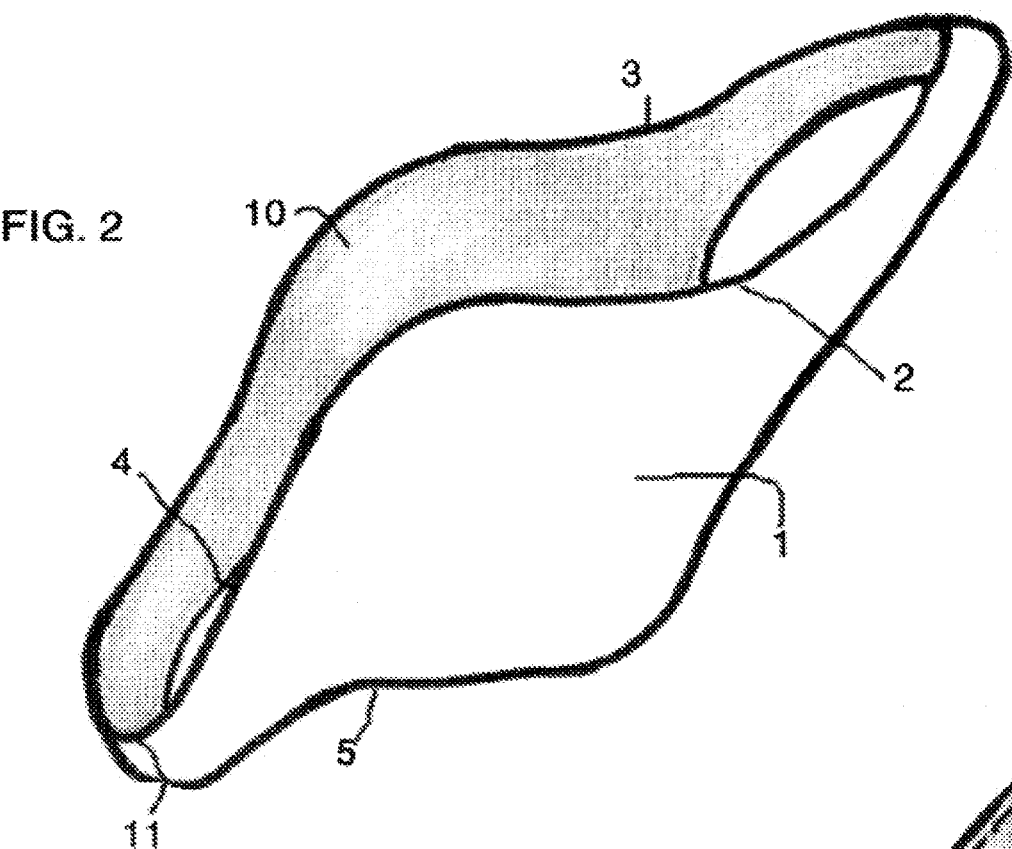
FIG. 2 is a view of a single layer construction of this Ear Protection Device. Both the inside and the outside of the device are visible from one side. The inside is shaded.

A single layer construction of this invention is indicated in FIG. 2. The numeral 1 indicates the outside, facing away from the individual wearing the device and 10, the area that is shaded, indicates the inside facing toward the individual.

The numerals 2 and 3 indicate the beginning of the front band and the beginning of the contouring of this band. The contouring gives this invention a shape that fits comfortably and securely along the hairline of an individual. There is not a set width for the bands. The same is true with the indications by numerals 4 and 5 that mark the beginning of the back band and the beginning of the contouring of this band which extends across the back of the neck at the hairline or from the location of the back of one of the ears of an individual and across the back of the neck at the hairline to the opposite ear of this individual.

The numeral 11 in FIG. 2 is the indication of a seam in the construction of this device. A seam is necessary but the location of this seam is of no consequence. Unless working with woven circular fabric or material in constructing this Ear Protection Device, a seam is necessary to form the circular construction.

Figure 3:
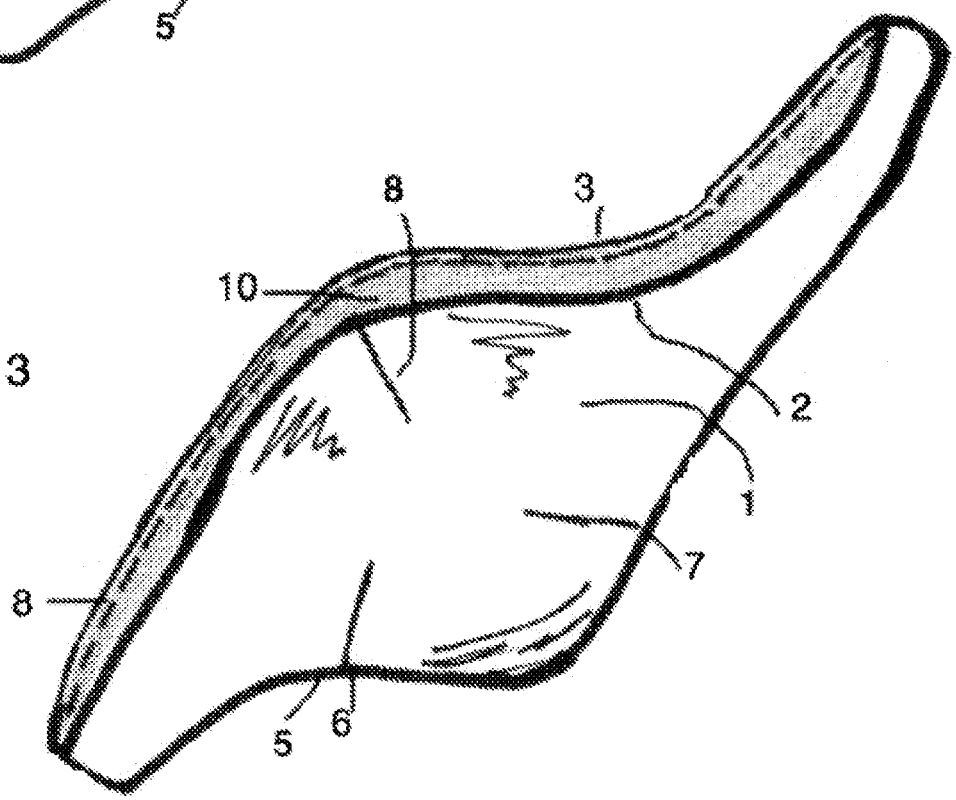
FIG. 3 is a view of this device with plural layer construction. The visible darts are one method of accomplishing the cupping of the area that covers the ear.

FIG. 3 represents this invention as constructed with a plurality of layers. The numeral 9 indicates a stitching together of these layers. Also in FIG. 3 darts are indicated by 6, 7 and 8. These darts are responsible for the cupping of the area that covers the ears of and individual wearing this device and assures a comfortable fit that does not tightly press the ears against the head of the individual. Extra layering can be in this area that covers the ear for the purpose of additional protection from the elements.

Figure 4:
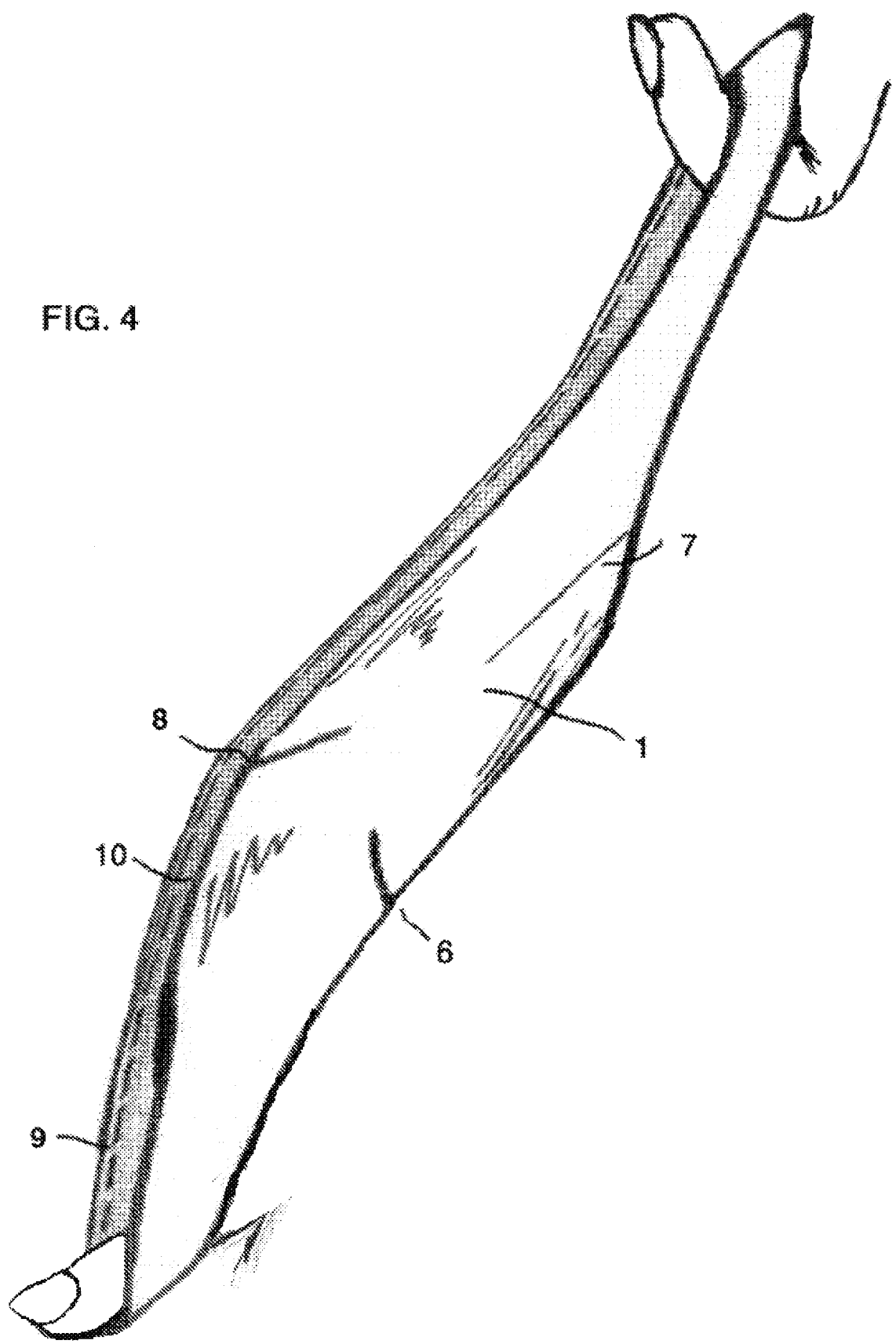
FIG. 4 is a view of the Ear Protection Device being stretched.

FIG. 4 is an example of the stretch in the circumference of this invention. The stretch as demonstrated in FIG. 4 is accomplished by the use of stretch fabric or material to construct the Ear Protection Device and/or by the insertion of elastic in the front and back bands. The purposes of this stretch are for the comfort of the individual wearing the device, for keeping the device in place along with the contoured construction, and for the ease of putting on or removing the device.

Figure 5:
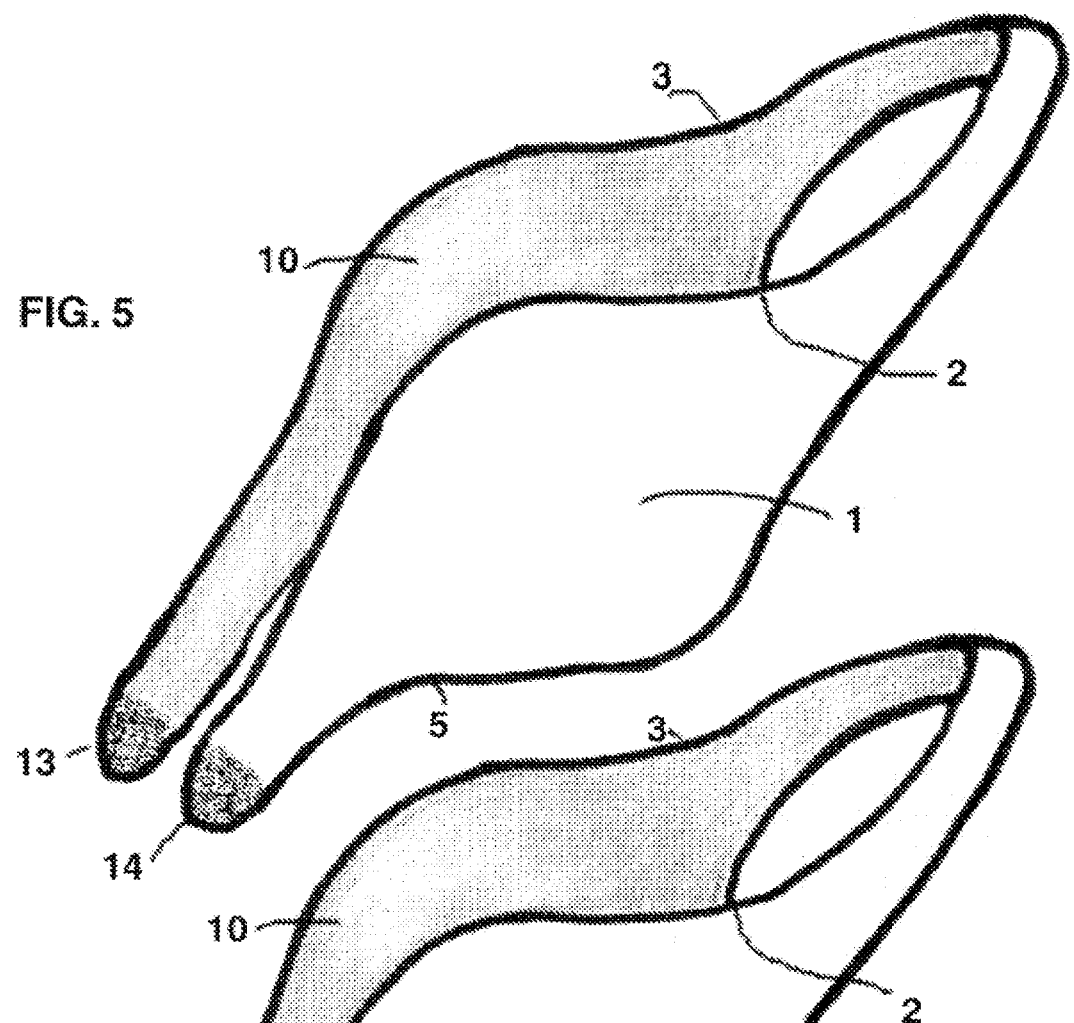
FIG. 5 is a view of the Ear Protection Device having and opening in the back with a Velcro closure.
Figure 6:
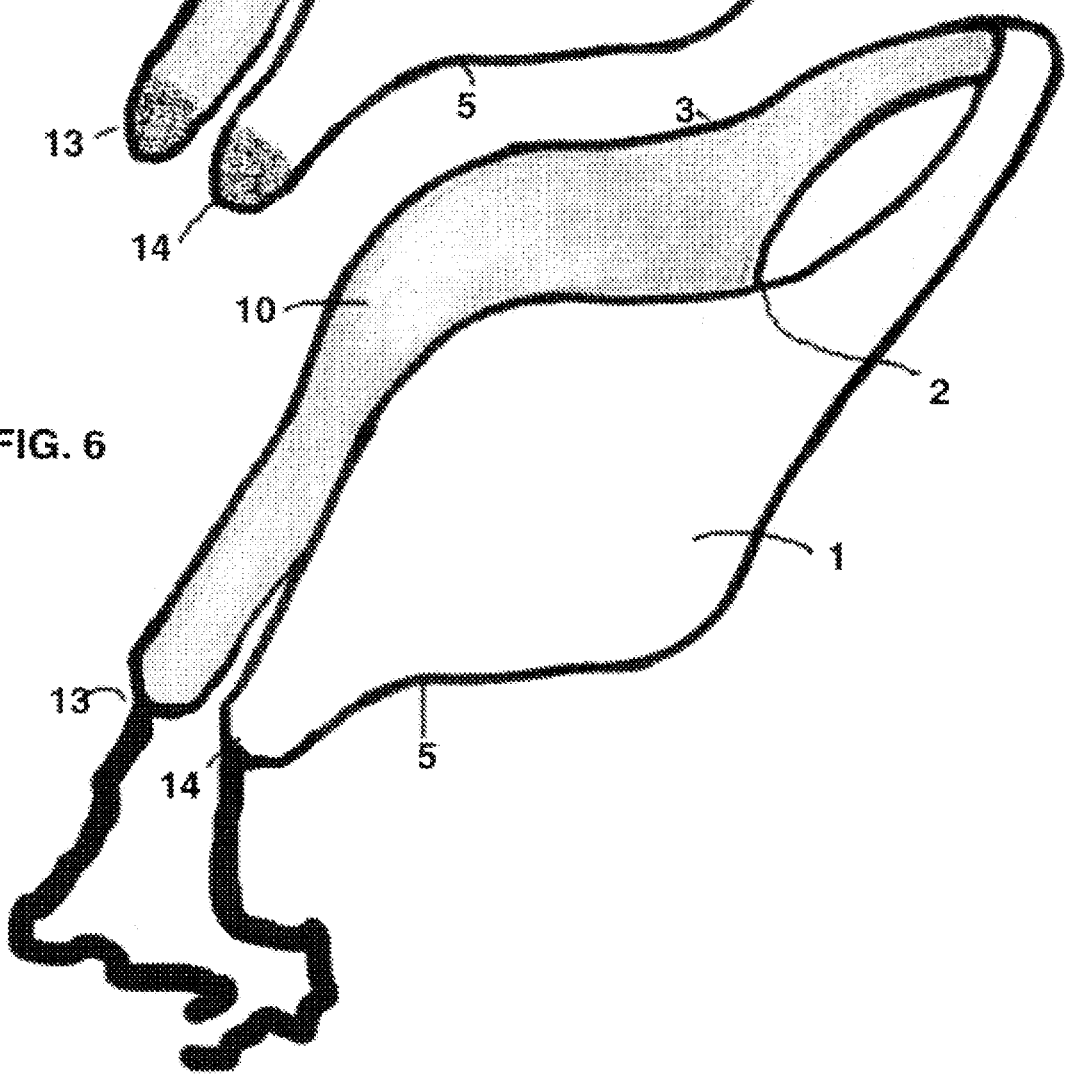
FIG. 6 is a view of the Ear Protection Device having an opening in the back with ribbons attached for the purpose of tying them together for closure.

FIG. 5 and FIG. 6 are examples of this invention wherein there is an opening at the midpoint in the back band of this invention. Each of the two ends of the opening indicated by 13 and 14 has a fastening device that adopts to cooperate in securing the ends together. If an opening is used in this invention, then it is not necessary to have the seam as indicated by 11 in FIG. 2.

FIG. 5 at 13 and 14 has Velcro as a fastening device on each end of the opening. FIG. 6 at 13 and 14 has sections of ribbon that are to be tied together as a fastening device.

FIG. 5 and FIG. 6 are two of the examples of fastening devices that can be used with this invention. Buttons, hooks and snaps are among the many devices that can also be used. In addition, the opening can be located anywhere on the front or back bands of this device.

Figure 7:
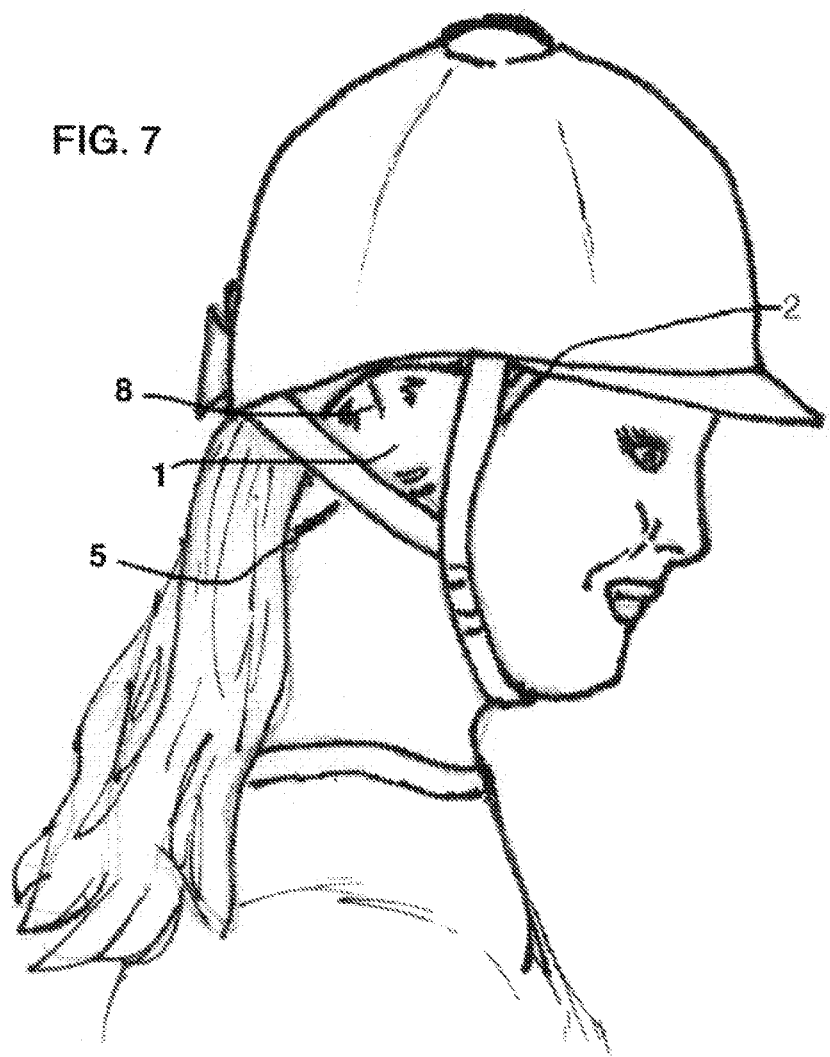
FIG. 7 is the view of an individual wearing an equestrian hardhat with the Ear Protection Device being worn under the hardhat.

FIG. 7 is an example of this invention being worn by an individual who is also wearing an equestrian hardhat. A part of the outside of the Ear Protection Device is visible and is indicated by the numeral 1. The very beginnings of the front band 2 and the back band 5 are visible. Also one of the darts 8 in the area that covers the ear can be seen.

Generally there is no protection from the elements for the ears of an individual wearing a safety helmet or hardhat. But generally a safety helmet or a hardhat is worn out-of-doors and the individual with certain weather conditions is exposed to the cold and the wind. The addition of this Ear Protection Device is comfortable under the safety helmet or hardhat and corrects the problem of the ears being exposed to the elements as indicated in FIG. 7.

Figure 8:
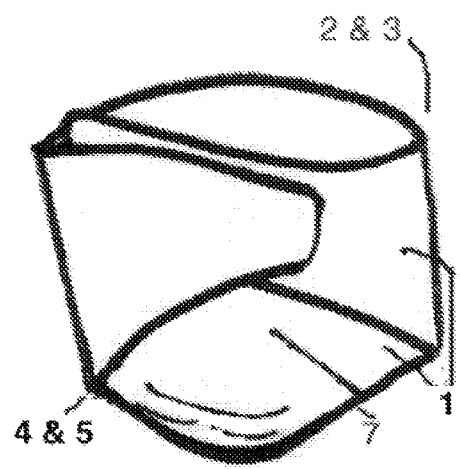
FIG. 8 is the view of a folded Ear Protection Device that is ready to be placed in a convenient place until needed.

The Ear Protection Device as shown in FIG. 8 is folded. The size and the flexibility is approximately that of a pocket-handkerchief. At this point the Ear Protection Device in FIG. 8 can be tucked away in a pocket or any convenient place.

Figure 9:
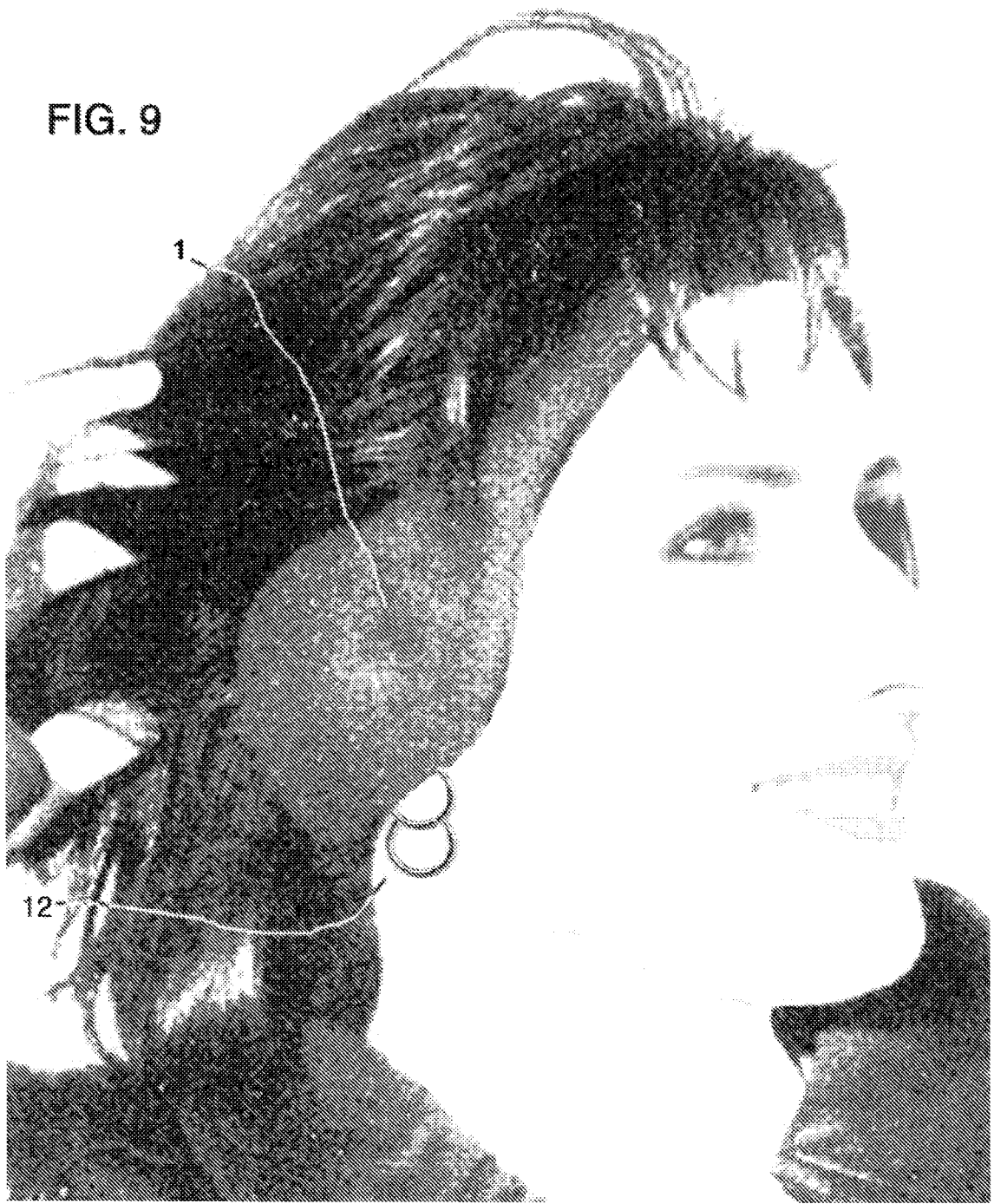
FIG. 9 is the view of an individual wearing the Ear Protection Device in conjunction with wearing ear jewelry.

FIG. 9 demonstrates an individual with ear jewelry 12 wearing this invention or Ear Protection Device. The fit of this device, the contouring and the stretch, is such that this invention can be worn comfortably with ear jewelry.

I claim:

1. A contoured ear protection device comprising:

a soft and pliable material having a variable width and having two ends connected together to form a loop comprising a front band having a first width, a back band having a second width, and two ear covering portions disposed circumferentially between the front and back bands, wherein each of the two ear covering portions has a third width that is greater than the first and second widths;

the device, when being worn over the ears of a user in a normal upright posture, having an equatorial plane bisecting the center of each ear covering portion parallel to the ground;

the front band being disposed above and forming a first angle with the equatorial plane and the back band being disposed below and forming a second angle with the equatorial plane;

the front band extending in a contoured manner at such an angle as to fit securely around the front of the individual's head along the edge of the forehead at the hairline and the back band extending in a contoured manner at such an angle as to fit securely around the back of the individual's head along the edge of the neck at the hairline; and said ear covering portions cupped to define a concave side over the ears and extending to and terminating at outer peripheral edges at their radial outermost extents.

2. The device of claim 1 wherein the cupping is accomplished by means of either (a) darts sewn in such a way as to cause cupping, or (b) the use of material or fabric that is woven or molded to cup, or (c) the use of stretch material or fabric that molds to pressure thus would cup over the ear as opposed to flattening the ear against the individual's head.

3. The device of claim 2 wherein, single or plural layers of soft and pliable material are used in the construction of the device.

4. The device of claim 3 wherein the ends of said length of material are connected together with fastening means, such that the ends may be selectively connected and disconnected by the user.

5. The device of claim 4 wherein the device is capable of being worn comfortably beneath a hardhat worn in sports or a hardhat worn for protection at work.

6. The device of claim 5 wherein the device can be folded when not in use.

7. The device of claim 6 wherein the device is contoured to closely fit the shape of the users head and to comfortably cup the user's ears without placing substantial pressure thereon and these two factors work together and make it possible to comfortably wear ear jewelry while wearing the device.

* * * * *